(12) United States Patent
Schmitz (10) Patent No.: US 11,453,175 B2
(45) Date of Patent: Sep. 27, 2022

(54) ANVIL ROLL WITH PROTRUSIONS WITH OUTWARDLY ORIENTED PINCHED WIRED ARCS

(71) Applicant: Concepts for Success (C4S), Euskirchen (DE)

(72) Inventor: Christoph Schmitz, Euskirchen (DE)

(73) Assignee: CONCEPT FOR SUCCESS, Euskirchen (DE)

( * ) Notice: Subject to any disclaimer, the term of this patent is extended or adjusted under 35 U.S.C. 154(b) by 200 days.

(21) Appl. No.: 16/767,063

(22) PCT Filed: Nov. 23, 2018

(86) PCT No.: PCT/EP2018/082422
§ 371 (c)(1),
(2) Date: May 26, 2020

(87) PCT Pub. No.: WO2019/101953
PCT Pub. Date: May 31, 2019

(65) Prior Publication Data
US 2020/0290289 A1 Sep. 17, 2020

(30) Foreign Application Priority Data

Nov. 24, 2017 (GB) .................................... 1719546
Jan. 31, 2018 (GB) .................................... 1801602

(51) Int. Cl.
| | | |
|---|---|---|
| *B29C 65/08* | (2006.01) | |
| *B29C 59/04* | (2006.01) | |
| *B29C 65/00* | (2006.01) | |
| *B29L 7/00* | (2006.01) | |

(52) U.S. Cl.
CPC ............ *B29C 65/086* (2013.01); *B29C 59/04* (2013.01); *B29C 66/1122* (2013.01); *B29C 66/41* (2013.01); *B29C 66/81453* (2013.01); *B29C 66/83411* (2013.01); *B29C 66/83511* (2013.01); *B29L 2007/008* (2013.01)

(58) Field of Classification Search
CPC ....... B29C 65/086; B29C 59/04; B29C 66/41; B29C 66/81453; B29C 66/83411; B29C 66/83511; B29L 2007/008
USPC ....................................... 156/580.2
See application file for complete search history.

(56) References Cited

U.S. PATENT DOCUMENTS

| | | | |
|---|---|---|---|
| 2,706,233 A | | 4/1955 | Yamaguchi |
| 5,242,529 A | * | 9/1993 | Riedel .................. B65B 51/225 156/580.2 |
| 2016/0056956 A1 | | 2/2016 | O'Hare et al. |

FOREIGN PATENT DOCUMENTS

| | | |
|---|---|---|
| EP | 1144187 A1 | 5/2000 |
| GB | 2504783 A8 | 12/2014 |
| WO | 2012042055 A1 | 4/2012 |

(Continued)

*Primary Examiner* — James D Sells
(74) *Attorney, Agent, or Firm* — Jordan IP Law, LLC (57) ABSTRACT

The present invention is a roll as may function as an anvil roll that comprises protrusions on its outer surface, that are outwardly or z-directionally oriented arcs of an arc wire such as wavy wire or an axially canted helical coil extending along a length or x-direction, which are pinched perpendicularly to the z- and x-direction. Such anvil rolls may be used to treat materials such as web materials, such as by embossing or bonding these web materials. In a particular application, such rolls may interact with an ultrasonic sonotrode.

18 Claims, 10 Drawing Sheets

(56) References Cited

FOREIGN PATENT DOCUMENTS

WO      2015165927 A1    5/2015
WO      2016166368 A1    10/2016

\* cited by examiner

ANVIL ROLL WITH PROTRUSIONS WITH OUTWARDLY ORIENTED PINCHED WIRED ARCS

FIELD OF THE INVENTION

The present invention is a roll as may function as an anvil roll that comprises protrusions on its outer surface, that are outwardly or z-directionally oriented arcs of an arc wire such as wavy wire or an axially canted helical coil extending along a length or x-direction, which are pinched perpendicularly to the z- and x-direction. Such anvil rolls may be used to treat materials such as web materials, such as by embossing or bonding these web materials. In a particular application, such rolls may interact with an ultrasonic sonotrode.

BACKGROUND

It is well known in the art to use rolls with protrusions on their outer surface, for example for treating web materials in embossing, bonding or printing processes. It is also known that protrusions exhibiting a rounded tip may be advantageous as an anvil acting against a heated or otherwise energy providing roll for certain applications, see e.g. EP1144187A1. However, the solution as described therein is difficult to manufacture, as it requires very laborious and hence expensive machining. For certain applications, for example in combination with ultrasonic bonding applications, it has been found to be advantageous to use protrusions with a rounded tip, that create an elongated imprint, see WO2012042055A1, wherein a flexible, preferably helical anvil roll is described, e.g., useful as an anvil in an ultrasonic bonding process, or WO2016/166368, wherein a rounded tip is used to displace particles in a web material. In US 2016/0056956, the making of canted coil springs, in particular with coil turns exhibiting alternatingly different diameter and dimension, for electrical applications is described.

The use of a flexible helical or coil spring anvil allows very simple application by allowing to use conventional, mass manufactured helical coil springs, and also provides several advantages both due to its flexibility and its geometric shape of the upper portion, i.e. the upper arc portion, of the coil spring. However, it has been found that such coil spring also flexes on the supporting surface of the roll, which may result in loss of bond force, mainly due to insufficient fixation of the coil spring. Hence there remains the problem of overcoming the described problem whilst maintaining the benefits especially of the geometric shape and easy manufacturing.

SUMMARY

The present invention is an anvil roll for treating a web material, preferably by heat embossing, more preferably for ultrasonic bonding. The anvil roll exhibits a cylindrical outer support surface, an anvil roll axis, and a radius, and comprises a plurality of arcs protruding outwardly of the cylindrical outer base surface, which are formed by an arc wire, preferably a metal wire, preferably essentially identical for the plurality of arcs, and more preferably a single wire forming the plurality of arcs.

The arcs comprise an upper free arc portion oriented outwardly of the support surface, such that the surface of the arc wire tapers down from its tip as the most outwardly positioned point of the free arc portion towards the anvil roll support surface in all directions, and a first and a second side arc portion. The plurality of arcs is arranged such that an arc tip line connecting the most outwardly positioned points of the upper arc portions defines the x-direction of the arcs. Each arc exhibits a length extension ($x_H$) along x-direction and an arc height $H_0$ extending perpendicularly to the support surface and to the length extension $x_H$.

Further, the anvil roll comprises a pinching device comprising at least two compression jaws positioned radially outwardly of the support surface, and adapted to apply a transverse compression force along a y-direction perpendicular to the length and height extension of the arcs at a pinch point in the side portions of the arcs, thereby essentially preventing movement of the anvil wire in the pinch point. Thus, the pinching device is adapted to transmit z-directional forces applied to the upper arc portion and via the first or second side portion through the pinch point to the support surface. Preferably, the arc wire exhibits a rounded cross-section, preferably circular or elliptic. Preferably, this cross-section extends at least at the most outwardly positioned points of the upper arc portions in the y-direction of the arc between 0.1 mm and 5 mm. The upper arc portion of the arcs may be circumscribed by an x-, z-directionally spanned circle of between 0.2 and 50 mm.

The x-directional distance of the most outwardly positioned points of the upper arc portions may be more than 0.1, preferably more than 1.0 times the free arc height $H_0$.

Preferably, the anvil roll is adapted to withstand z-directional impact on the arcs under use conditions such that these deform z-directionally less than 20μ, preferably less than 10 μm, most preferably less than 5 μm.

The pinching of the arc wires may be executed in several ways:
- the arc wire is pinched at a single pinch point wherein two wires are crossing;
- the arc wire is pinched at two pinch points or pinch areas, each one in each of the side portions wherein a single wire is pinched;
- the arc wire is pinched at three pinch points, with two pinch points in the side portions, wherein two crossing wires are pinched, and a single pinch point wherein two wires are crossing, the single pinch point being positioned between the other two pinch points and the support surface;
- the arc wire is pinched such that each two directly neighboring arcs have two common pinch points.

The arc wire may be essentially continuous for the plurality of arcs. The anvil roll may comprise two or more arc wires, preferably aligned parallel to each other. The anvil wire may be a canted coil spring, preferably exhibiting a pitch that is more than 0.1, preferably more than 1.0 times the free arc height $H_0$, or a wavy wire, preferably exhibiting a distance between the most outwardly positioned points of the upper arc portions of two neighboring arcs that is more than 0.1, preferably more than 1.0 times the free arc height $H_0$.

Optionally, the anvil roll may comprise two or more wavy wires positioned parallel between one pair of compression jaws and such that their tip lines are essentially parallel and their tip points are x-directionally offset.

The x-direction of an arc wire may be essentially aligned parallel to the anvil axis, or circumferentially to the anvil surface, wherein preferably the compression jaws are ring discs, or disc elements being integral parts of the anvil roll, and wherein the pinching device further comprises a compression means that is adapted to act on the compression jaws simultaneously, and wherein preferably the arc wire is essentially endless.

BRIEF DESCRIPTION OF THE FIGURES

FIGS. 7A and B depict an anvil roll comprising a canted coil spring according to the present invention.

Same numerals refer to same elements or features. The figures are schematic and not necessarily to scale.

DETAILED DESCRIPTION

In the following description, the explanation of the present invention may refer to specific executions or embodiments, and may refer to certain elements in combination with other elements, which, however, should not be seen to limit the present invention to these executions, embodiments, or combinations.

Generally, the present invention is directed towards an anvil roll that may very suitably be employed for creating embossing or bonding of web materials. Such an anvil may be a rotating roll that interacts with a counter-tool, as may be a counter-rotating roll, or a flat part, such as a static flat horn of an ultrasonic unit. Often, though not necessarily, either one or both of the anvils may comprise an energy source, such as heating or kinetic energy supply such as from an ultrasonic system. For such applications, it may be very desirable to have at least one of the anvils exhibiting protrusions on its outer surface that may interact with a work piece, such as a web material.

Without wishing to limit the applications by the following, possible applications may be:

Creating patterns of embossing points by pressurizing web materials with a pattern of embossing points made by the protrusions of one or both of the anvils.

Such embossing may comprise melt-fusioning the web material in the embossing or bond points;

Creating bonding between two or more web materials, preferably by melt-fusioning of web materials comprising melt-fusion compatible compounds with a two-dimensional or a linear pattern.

Creating particle free regions in particle loaded fibrous webs—as described in WO2016/166368. For such applications, it is often desirable to have a small embossing point area, and in case of bonding, that these exhibit a gradual transition from strongly treated regions of the bond-points towards non-treated regions surrounding these bond points, as described for example in the above-mentioned WO2011/042055.

Henceforth the present invention provides an anvil roll that exhibits protrusions on its outer surface that have a rounded tip and a surface tapering away in all directions. The outwardly oriented tips of the protrusions may exhibit a certain flexibility, for example to allow to operate the anvils at a certain small interference, i.e. the axes of two anvil rolls are spaced apart less than the sum of the outer radii, which correspond to an enveloping surface of the anvil around its protuberances. An anvil roll may be sized according to the specific application, and may exhibit a diameter of more than about 0.05 m up to about 1 m.

As known from the previously cited prior art, it is known that helical springs may suitably be employed for such applications. However, and without wishing to be bound by the theory, it is believed that the flexibility of the helical spring may induce flexing and possibly uncontrolled movement of the spring on its support. In particular, if the anvils are operated at a certain interference or the web materials in the gap between the anvils fill the gap width to a substantial part, the first force transmitting contact might not be at the tip of the protrusion but slightly before along the direction of relative movement, thusly inducing a small but unbalanced torque that may twist and turn the spring.

An anvil according to the present invention has a roll shape, and thusly exhibits an anvil roll axis and a cylindrical outer surface at the radial distance r from the axis, whereby r may range from about 1 cm to about 100 cm. The width of the anvil along the roll axis is adapted to the intended use, and may range from 1 cm to about 2 m, though even wider rolls of typically less than 10 m are not excluded. The rotatably mounted anvil roll may be driven by conventional means, such as servo drives.

The anvil roll according to the present invention comprises protrusions on its outer surface, which exhibit
  a rounded tip tapering in all directions away from the enveloping surface;
  sufficient rigidity to withstand radial compression forces while maintaining a higher flexibility, compared to a standard solid anvil roll;
  good fixation on the support surface of the anvil roll.

This is achieved by positioning a plurality of arcs on the support surface of an anvil roll. Within the present context, the term "arc" refers to a structure formed by an arc wire such that it has a rounded tip or free arc portion that is positioned most outwardly from the support surface, and two side portions that extend from the free arc portion towards the support surface.

The free arc portion may have a rounded shape such that a circumscribing circle exhibits a diameter. Within the present context, the term "arc wire" refers to a wire made from a material suitable for the intended use, and preferably is metallic, such as steel, preferably spring steel, or the like. The arc wire preferably exhibits a rounded shape, at least for the free arc portions, and may have a circular or elliptic cross-section, thusly creating the tapering from the arc tip in all directions towards the support surface. The arc wire may suitably exhibit a size of from about 0.1 mm to about 4 mm.

The plurality of arcs comprises at least two, often between 10 and 100 arcs, and typically less than 2000 arcs. Connecting the tips of the arcs forms an arc line that preferably is a straight line, such as parallel to the anvil roll axis, or a circle, such as parallel to the cylindrical outer anvil surface, so as to ease the design of the pinching device, or a circular arc with a radius larger than the radius of the supporting roll, as described in more detail herein below. The arc line defines the length or x-direction of the arcs. The height or z-direction of the arcs extends along the radial direction of the anvil roll away from its axis, and the height $H_o$ is the distance of the most outwardly point, or tip, of the arc towards the support surface. The x-directional distance of two neighboring arc tips may be more than 0.1, often more than 1.0 times the arc height.

The anvil roll may comprise one or more than one plurality of arcs, which preferably are arranged parallel to each other, respectively, such as when several straight arc lines are positioned in a configuration parallel to the anvil axis, or when several circular lines are arranged next to each other. The distance of two neighboring arc lines may be from about 1 mm to 1 m or more, e.g., when a bond line formed by arcs corresponding to the arc line, is just at the lateral side edges of a substrate run through the anvils. Often, the distance is between about 2 mm and about 30 mm.

The anvil roll further comprises a pinching device for firmly holding the arcs in place, which comprises at least two compression jaws, positioned opposite to each other in the width direction, i.e. perpendicular to a x-z-plane, of the plurality of arcs and adjacently thereto. The compression jaws may also be integral parts of the anvil roll, as achieved by cutting slits into the anvil roll which may house the lower arc portions. The pinching essentially aims at preventing movement of said arc wires at the points of contact between the arc wire and the compression jaws, also referred to as pinch points, whereby, as will be explained in more detail, a single wire or two crossing wires may be pinched in one pinch point. The skilled person will readily realize that—especially when the arc wire exhibits a flat surface towards the compression jaw—the pinch point may not be a point in the strict mathematical sense but may cover a certain though well delimited pinch area on the wire(s) and/or the compression jaws.

Thus, the pinching device is adapted to transmit z-directional forces applied to the upper arc portion via said first or second side portion through the pinch point(s) to said support surface. Under such z-directional forces during use, the arc tips reposition preferably less than about 20 µm, more preferably less than about 10 µm and even more preferably less than about 5 µm. The arcs may, and often do comprise lower arc portions extending from the pinch points towards the support surface, and may—and often do—rest thereon. In preferred executions the arc wire of the lower arc portions of two neighboring arcs are essentially continuous, or even all arcs of the plurality of arcs may be formed from a single continuous arc wire that runs from an arc to a neighboring arc through the lower arc portions.

Preferably the compression jaws extend in the x-direction so as to pinch all arcs of the plurality of arcs, though a plurality of compression jaws arranged along the x-direction may be employed.

In case of the anvil roll comprising more than one plurality of arcs, each may be combined with a pair of compression jaws. Alternatively, a compression jaw may be positioned between and cooperate with two neighboring plurality of arcs, or several plurality of arcs may each be separated by a compression jaw, which are all compressed together by two outer compression jaws activated by a compression means.

Depending on the specific execution as described herein below, for each arc one of the conditions applies that is selected from the group consisting of
  a. the wire is pinched at a single pinch point wherein two wires are crossing;
  b. the arc wire is pinched at two pinch points or pinch areas, each one in each of the side portions wherein a single wire is pinched;
  c. the arc wire is pinched at three pinch points, with two pinch points in the side portions, wherein two crossing wires are pinched, and a single pinch point wherein two wires are crossing, the single pinch point being positioned between the other two pinch points and the support surface;
  d. the wire is pinched by four pinch points, each two in each side portion, wherein two wires are crossing.

Figure 1A:
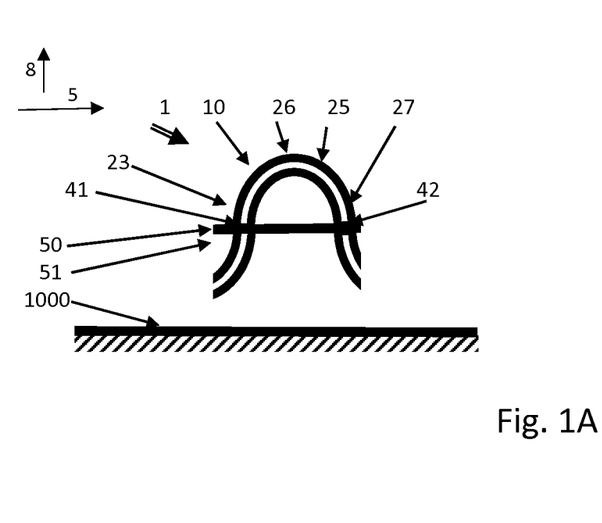
FIG. 1A to C depict wire arcs as may be useful for the present invention.
Figure 1B:
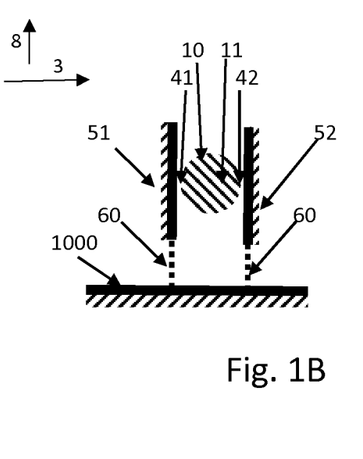
Figure 1C:
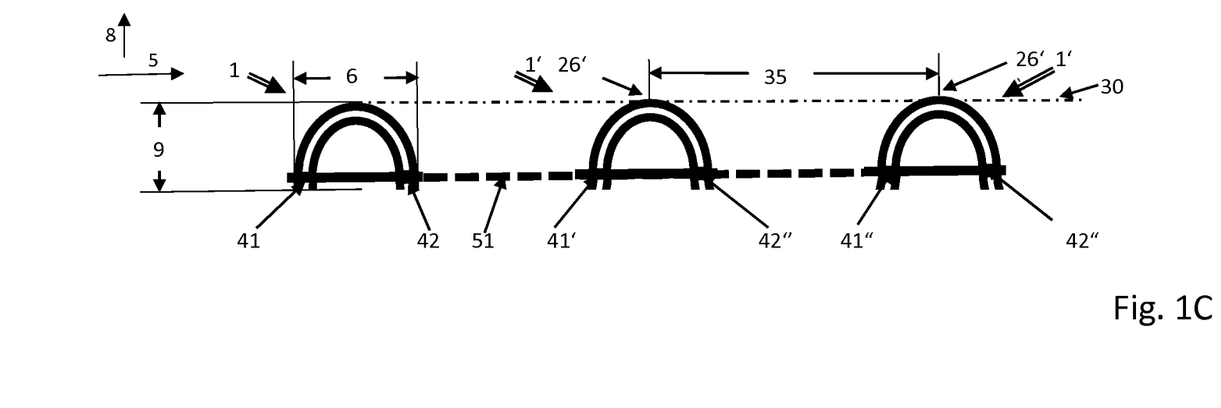

FIG. 1A to C depict schematically the principle of the present invention, showing an arc wire 10 of an arc 1, with an upper arc portion 25 and the arc tip 26 as the point which is most outwardly positioned relative to a support surface 1000. Further, the arc comprises a first (23) and a second (27) side portion tapering from the arc tip towards the support surface 1000. The arc wire 10 exhibits a rounded cross-section 11, as shown exemplarily in the cross-sectional view in FIG. 1B. As further shown in FIG. 1C in Cartesian coordinates with a z-direction 8, a length direction 5 and a width direction 3, the arc exhibits an arc height 9 and an arc length 6. Further, FIG. 1C shows schematically a plurality of arcs 1, 1', 1", as may be space apart in x-directionally by arc distance 35 from the tip 26' of an arc 1' to the tip 26" of a neighboring arc 1". The tips, or most outwardly oriented points of the arcs, 26, 26' . . . form an arc tip line 30, here shown as a straight line.

In FIG. 1A to C, the pinching of the arcs is depicted by showing compression jaws 51 and 52, respectively, of a pinching device 50, extending length directionally along the arc (FIG. 1A) and plurality of arcs (FIG. 1C), respectively. The compression jaws pinch each first and second side portion of each arc firmly at the pinch points, 41, 42, 41', 42', 41", 42", respectively. As indicated in FIG. 1C by the dashed line of pinching jaw, a pinching jaw 51 may extend over several all arcs of the plurality of arcs. The compression jaw is connected by connection 60, as may be integral with the compression jaw or the support 1000, to the support 1000 and adapted to transmit forces from the arc to the support in any conventional manner, or the compression jaw is an integral part of the anvil roll. For the execution as indicated in FIG. 1B, there is only a single arc wire 10 between the compression jaws 51, 52 at the pinch points 41, 42 that are then distanced from each other essentially at the y-directional extension or thickness of the arc wire.

Figures 2A, 2B:
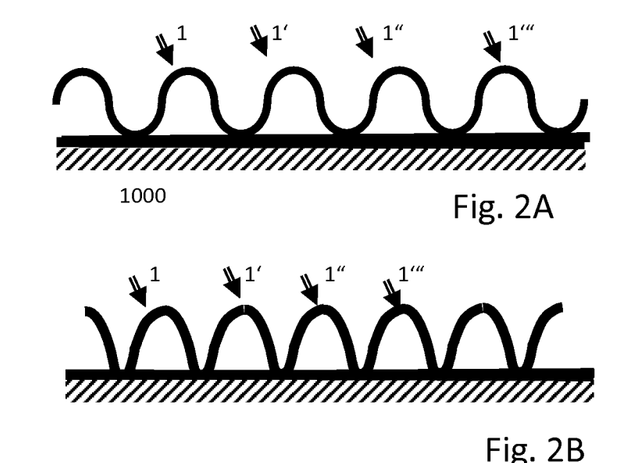
FIG. 2A to G depict various executions for wavy wires as arc wires useful in the present invention.
Figure 2C:
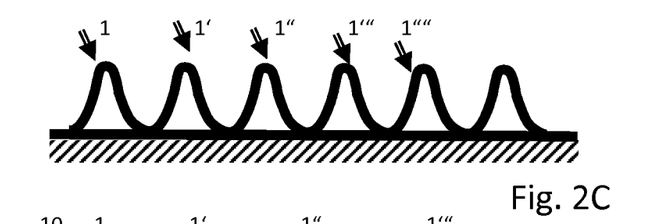
Figure 2D:
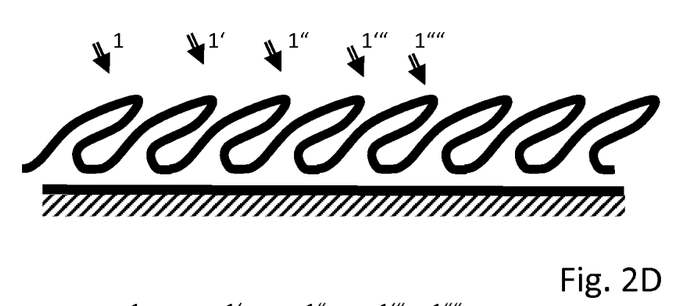
Figure 2E:
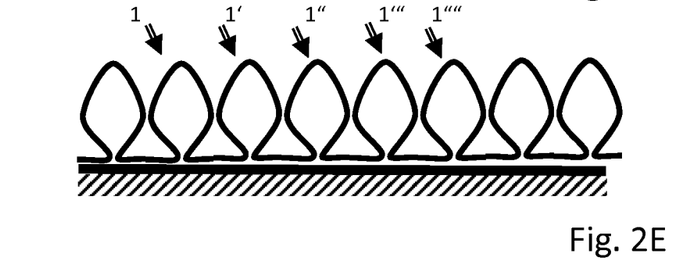
Figure 2F:
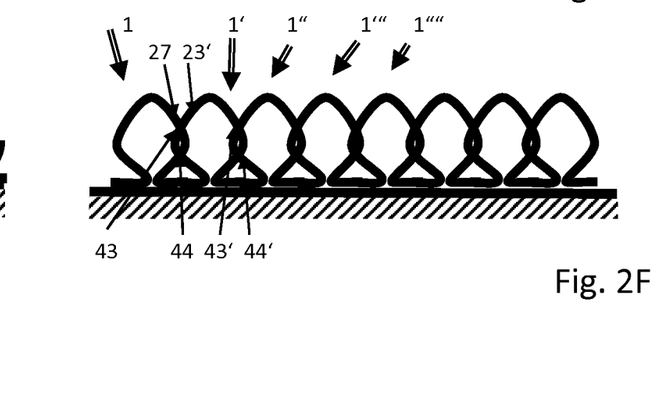
Figure 2G:
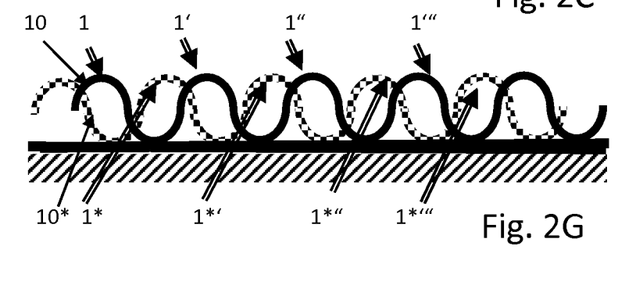

FIG. 2A to F depicts several executions of a plurality of arcs, as may be realized by shaping a continuous arc wire. In FIG. 2A, the arc wire is in the form of a "wavy wire", showing a plurality of three arcs 1, 1', 1" in a sinusoidal like arrangement with about evenly rounded arcs oriented outwardly and towards the support 1000. When looking from a z-direction, the wavy wire would be essentially straight. As FIG. 2B shows an execution of a differently shaped wavy wire, wherein the outwardly positioned arcs exhibit a relatively larger radius than the ones towards the support 1000, whilst in FIG. 2C, the outwardly oriented arcs are smaller than the lower ones. In FIG. 2D, the arcs are not symmetric along their length direction, and FIG. 2E shows Ω-shaped arcs, spaced apart such that the side portions are still distanced. FIG. 2F depicts a further option for pinching, when an Ω-shaped wavy wire is employed that is similar to the one of FIG. 2E, however the arcs are moved x-directionally closer to each other, such that a second side portion 27 of arc 1 overlaps with the first side portion 23' of the neighboring arc 1'. In such an instance, there are each two pinch points 43 and 44 shared by two neighboring arcs. It should be noted that for both pinch points 43 and 44, the same wire portion, e.g., the second side portion 27 of arc 1, lies over the same other wire portion, here of the first side portion 23' of the arc 1'. FIG. 2G depicts yet a further execution, wherein two straight wavy wires are positioned parallel offset between compression jaws, as shown exemplarily such that a first wavy wire 10 has its arcs 1, 1', 1", 1'" offset from the arcs 1*, 1*', 1*", 1*"" of a second wavy wire 10*.

Figures 3, 3D:
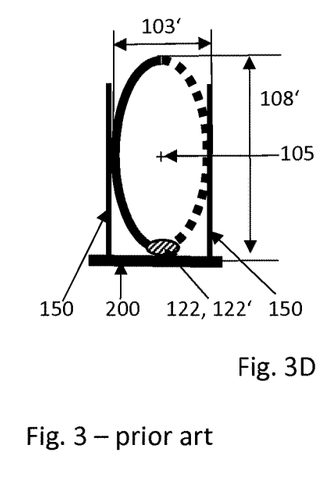
FIG. 3A to D depict the geometry of a conventional helical coil spring.

The plurality of arcs may further be formed from a canted coil spring. For explaining the general nomenclature of coil springs, reference is made to FIG. 3A to C, wherein a non-canted helical coil spring 100 with its spring wire 110 is depicted in a side view (FIG. 3A), i.e. looking in Cartesian coordinates from a y- or width direction onto such a spring extending along its x-directional or longitudinal axis and centerline 105 and its height 108, such as when being positioned onto a support 200 extending in the x-y-dimension (10, 20). The coil spring is made up of a series of turns 120, 120', . . . , distanced apart from each other by the pitch 135. For ease of visualization, in FIG. 3A, the "rear" half portions 138 of the turns of the coil spring 100, i.e. the half portions behind the center line relative to a viewer's position are plotted as dotted lines and the "front" half portions 133 as solid lines. FIG. 3B depicts a coil spring in a top view, further showing the width 103 of the coil spring, and in FIG. 3C, the view is along the centerline.

Figure 3A:
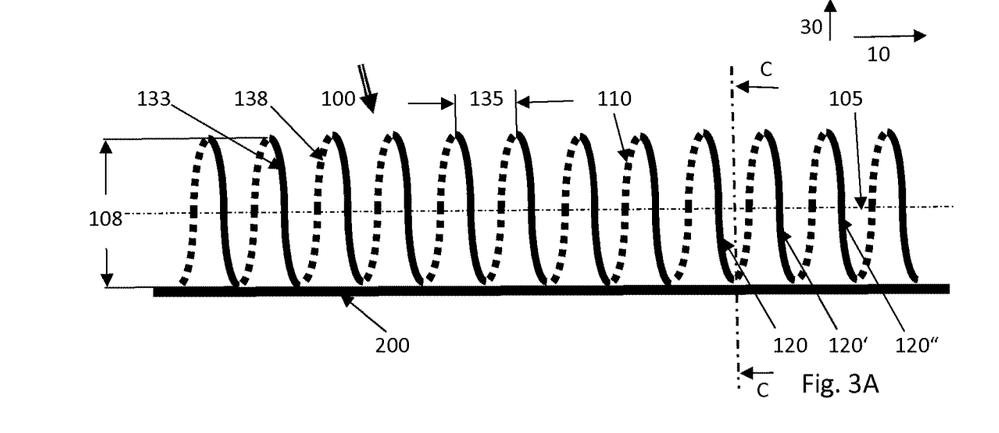
Figure 3B:
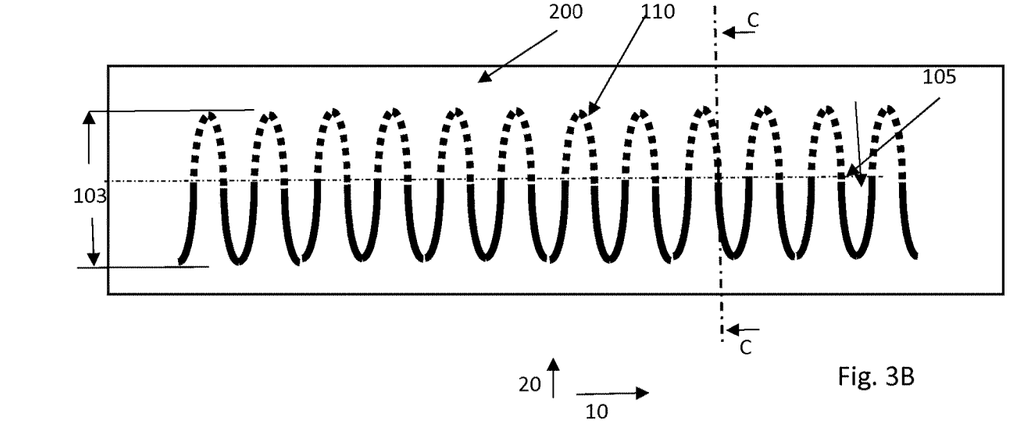
Figure 3C:
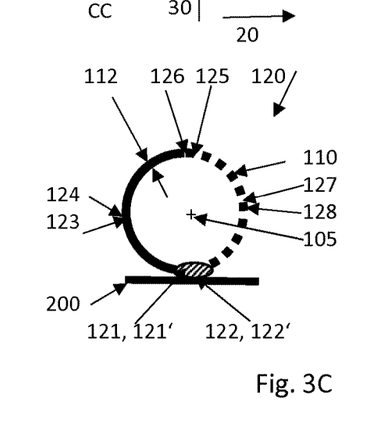

As can be seen in FIG. 3C, each one turn 120 comprises further characteristic portions, each with a radially most outward point, namely
 a lower arc portion 121 with a first lowermost or contact point 122 of the wire with the support,
 a first side arc portion 123 with radially, and here also laterally, most outwardly positioned first side point 124,
 a top arc portion 125 with the uppermost arc point or arc tip 126,
 and a second side arc portion 127 with a laterally most outwardly positioned second side point 128,
 a further lower arc portion 121' where the turn 120 connects to the further turn 120' with the second lowermost or contact point 122 of the first turn 120 coinciding with the first lowermost or contact point 122' of the next turn 120'.

Thus a lower arc portion extends in both x-directions from the lowermost point into two consecutive turns of the coil spring. In FIG. 3C, the lowermost region 122 is shown shaded, indicating that the view is made at a cross-section through the wire 110 at the first lowermost point 122' of the next turn 120'.

As shown, the coil spring exhibits an essentially cylindrical shape, wherein the height 108, i.e. the distance of the lowermost point 122, which is in contact with the support 200, to the uppermost arc point 126 is the same as the width 103, i.e. the distance between the two most outwardly positioned points 124, 128, respectively. If such a spring coil is compressed y-directionally, e.g. by a pair of x-z-directionally extending jaw planks 150 as shown in FIG. 3D, the wire will deform such that each turn is compressed from its essentially circular shape into an elliptical shape with an increased height 108' and reduced width 103'.

Figure 4A:
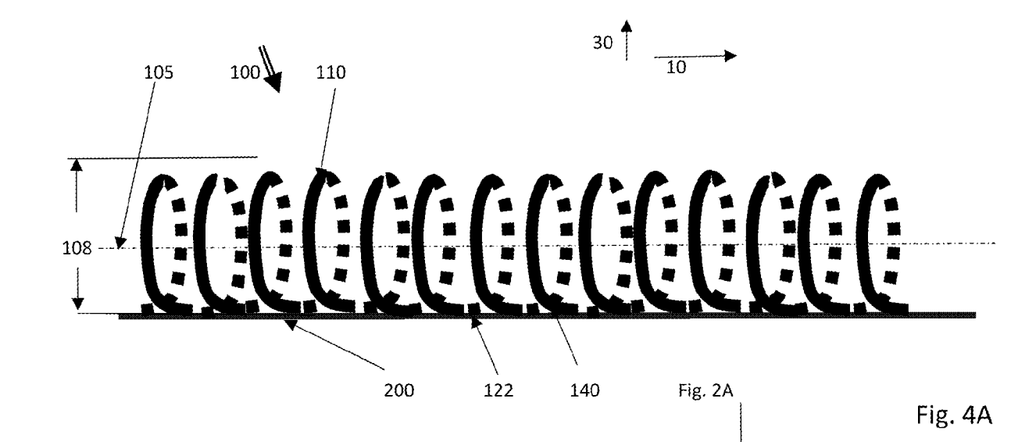
FIG. 4A to F depict the geometry of a canted coil spring in an axial configuration, as may be useful for the present invention.
Figure 4B:
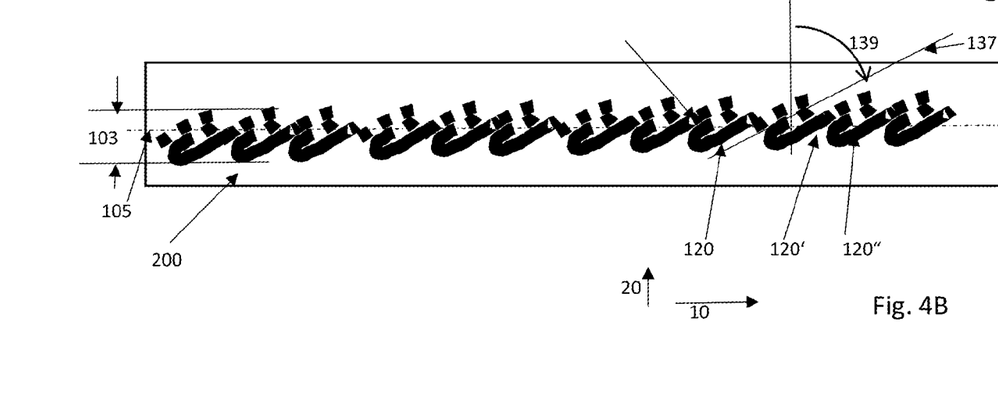
Figure 4C:
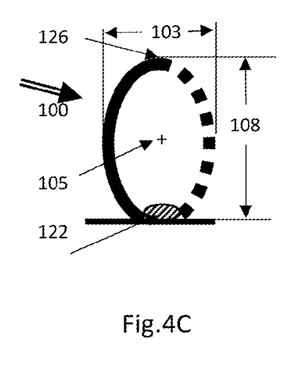

When considering a canted coil spring useful for the present invention, sometimes also referred to as slanted coil spring, the same definitions apply—as can be seen in FIG. 4A to 4C, showing such a canted coil spring in analogy and with corresponding nomenclature to FIG. 3A to C. In a side view as in FIG. 4A, i.e. along the y-axis onto an x-z-plane, the wire can be seen as overlapping loops. In FIG. 4B, showing a view from the z-direction, the wire can be seen in a meandering shape. In a side view along the x-axis onto a y-z-plane, see FIG. 4C, the wire shows an elliptical shape. The degree of the canting can be described by the axial canting angle $\gamma$ 139 which is defined as the angle of a canting plane and a z-y-extending plane 137 through a lowermost or contact point, whereby the canting plane is spanned by
 the lowermost point where turn 120' joins turn 120,
 the midpoint between the first side points of a previous turn 120 and turn 120',
 the midpoint between the second side points of the turn 120 and a subsequent turn 120'.

Thus, the canting angle describes the degree of canting, and has its minimum for a non-canted coil as shown in FIG. 3, and reaches its maximum ($\gamma_{max}$) when the side portions of the wire of adjacent turns are touching each other at a pinch point 140 and as such is a function of the diameter of the coil wire and the pitch 135. It is always smaller than 90°.

It should be noted, that upon application of a transversal force, a canted coil spring behaves substantially different from a non-canted coil spring, that deforms as shown in FIG. 3D, where the width 103' of the coil is reduced by compressing the coil whilst increasing its height to an increased compressed height 108', i.e. deforming a circular cross-section of a coil to an elliptical one, whilst for a canted coil spring the width is reduced, and the canting angle enlarged until $\gamma_{max}$ is reached.

Figure 4D:
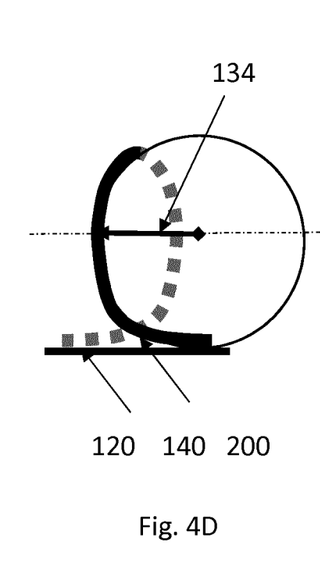
Figure 4E:
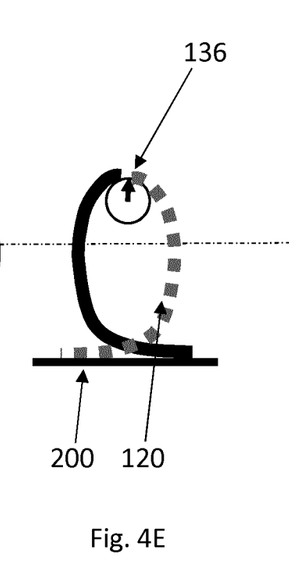
Figure 4F:
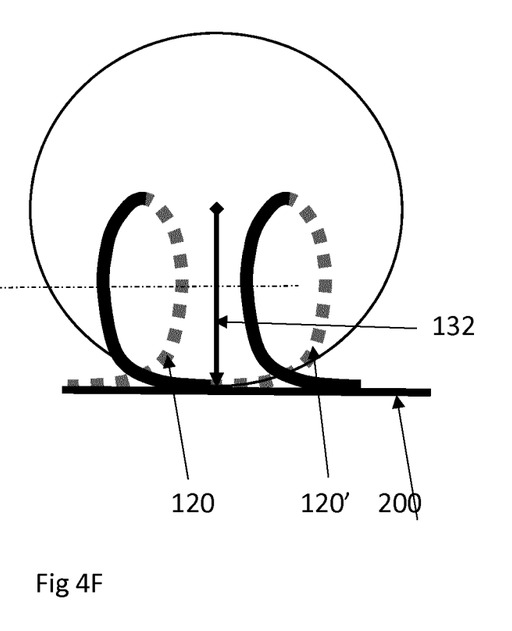

In comparison to a non-canted coil spring, a canted coil spring does not show even radii along one full turn. When considering the inscribed circles at the characteristic portions of a turn of a canted coil in a preferred execution, a canted spring coil exhibits for the side portions point 123 and 127 a radius 134 (see FIG. 4D) that corresponds about the height of the canted coil spring, also corresponding about to the radius of a non-canted cylindrical coil. At the uppermost and lowermost points, the radii of the inscribed circles are quite different, e.g. for the lowermost portion 121 the radius of the inscribed circle 132 is larger (see FIG. 4F), and for the uppermost portion 125 the radius 136 is smaller, (see FIG. 4E). The skilled person will readily realize, that also the opposite configuration is possible and suitable for the present invention, whereby the smaller inscribed circle is positioned towards the support 200, and the larger one outwardly.

Figure 5A:
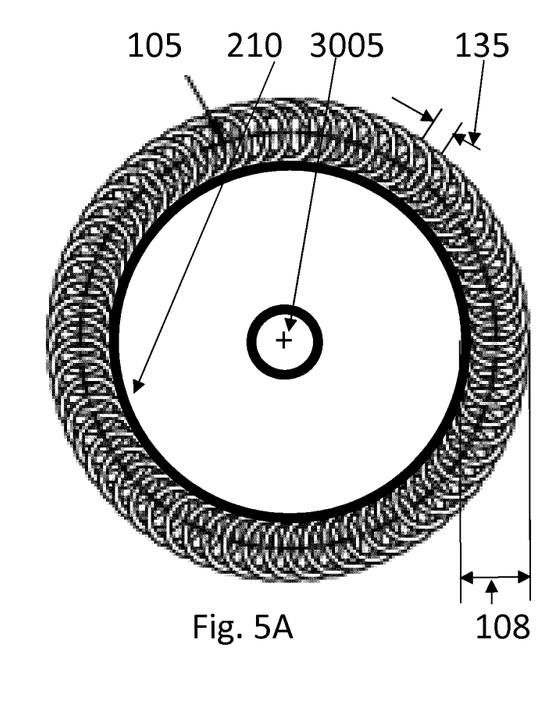
FIG. 5A depicts a canted coil spring in an axial configuration, though exhibiting a less preferred execution with a low pitch to height ratio.

As shown in FIG. 4, the canted coil spring exhibits a pitch 135 that is preferably more than the height, as then only one pinch or crossing point 150 as seen in FIG. 4B occurs. In FIG. 5A an execution is depicted for an axially canted coil spring, for which the pitch 135 is smaller than the height 108, such that there are—in the view of FIG. 5A—more than one crossing point of the wire for each one turn.

A skilled person will also readily realize, that a canted coil spring can be positioned on a non-flat surface, but, for example shown in FIG. 5A, wound around the surface of cylindrical roll or drum 210, especially if the diameter of the roll is large compared to the diameter of the spring, as indicated in FIG. 5A. Such a roll exhibits a cross-directionally oriented roll-axis 3005 around which the roll is rotatably mounted and the rotation defines the machine direction of the roll. In cylindrical coordinates, the radial direction extends away from the axis, and a cylindrical surface of the roll may form the support for the canted coil.

Figure 5B:
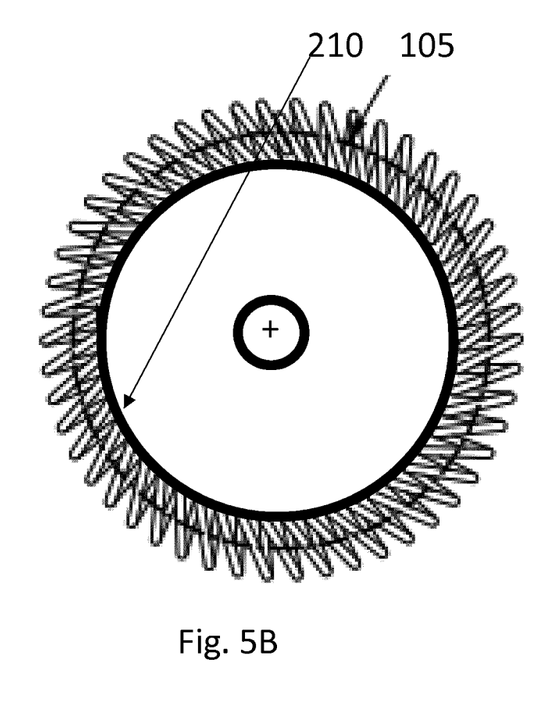
FIG. 5B depicts a canted coil spring in a radial configuration, as being not useful in the present invention.

As shown in FIG. 5B, a canted coil spring in a radial configuration is not suitable for the present invention.

Figure 6A:
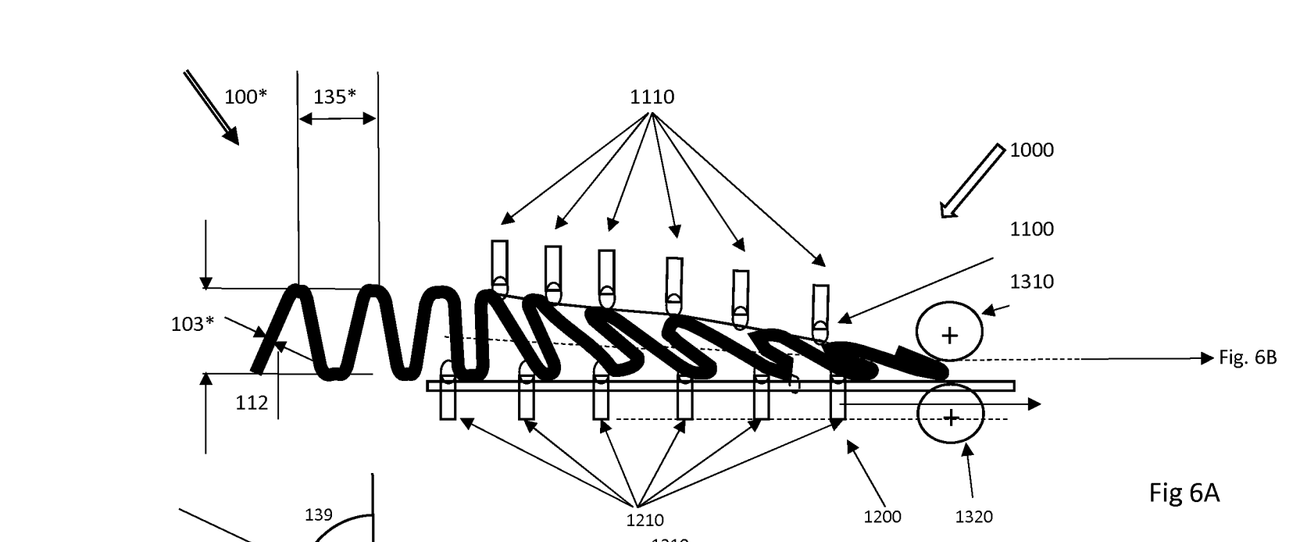
FIGS. 6A and B depict an equipment relating to a process for making a canted coil spring suitable for the present invention.
Figure 6B:
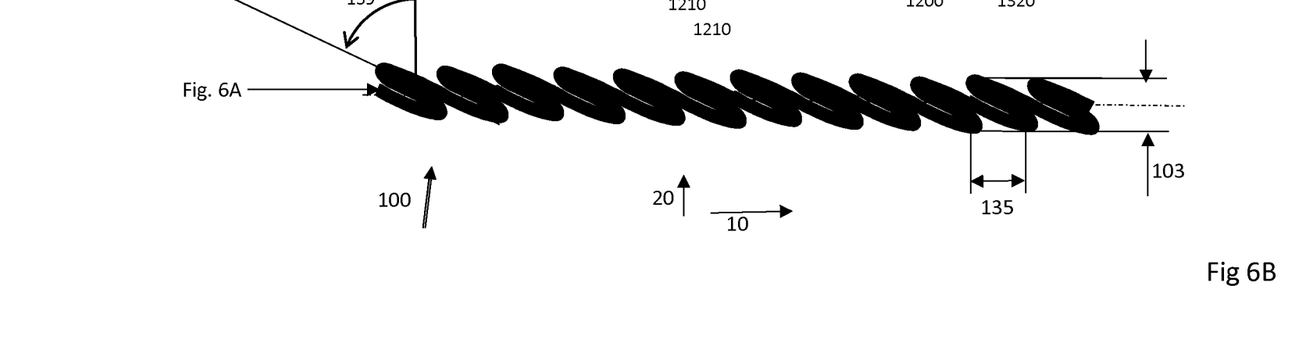

A person skilled in the art will readily recognize that an axially canted coil spring can have a forward canting, wherein the angle γ is positive relative to the x-direction of the center axis, such as depicted in FIG. 4B, or it can have a backward canting, wherein the angle γ is negative relative to the x-direction of the center axis, as depicted in FIG. 6B.

The material selection for the canted coil spring is not particularly limited, however materials as conventionally employed for mechanical springs, such as stainless steel or similarly strong and resilient metallic material are preferred.

Suitable axially canted coils are commercially available from NPI spring, CO, US, under the trade designation "Axially Compressed Dynaflex™" for electrical or sealing applications. However, it is not preferred that they exhibit a small pitch and as shown in FIG. 5A, and thusly do not show the larger difference of the radii of the upper inscribed circle 136 and lower inscribed circle 132 as shown in FIGS. E and F.

A suitable canted coil can be manufactured with a tool and a process as depicted schematically in FIGS. 6A and B. Therein, a non-canted precursor spring 100* with a wire diameter 112 and a precursor pitch 135* is provided, optionally formed in-line just prior to the present process steps. The precursor spring is moved into the gap of a canting tool 1000 comprising a stationary tool 1100 and a moving tool 1200, which both have guide means e.g., in the form of teeth 1110 and 1210, that are longitudinally spaced according to the pitch of the precursor coil, respectively. The moving tool may be an essentially endless belt or wire with outwardly extending teeth, or may be a helical screw type feeder ("worm"), the teeth of which being adapted to receive a side portion of the coil and to transport it along the direction of movement of the coils. The stationary tool is spaced apart from the moving tool at a decreasing distance of its surface and/or teeth at a starting distance that may correspond to the width (and height) of the precursor coil, and will be reduced to essentially corresponding to a width close to the width of the canted coil, optionally further supported by additional compression roller 1310, 1320.

It should be noted, that two options for executing the canting can be followed. For the first, the uppermost and lowermost point of a turn is engaged with fixation means of the tools, respectively. The repositioning one of them relative to the other along the x-direction provides the desired canting. For the second, the two laterally and oppositely most outwardly positioned points of a turn are engaged with the fixation means and repositioning them relative to the each other along the x-direction provides the desired canting. Both options provide canted coil springs that are suitable for the present invention, however require appropriate mounting on the base anvil so as to provide the appropriate canting angle.

The result is a canted coil, which may be essentially endless, or which may exhibit a predetermined length, which may further be connected by conventional means so as to form a longer coil, or also a closed ring coil, exhibiting an inner coil ring diameter. Typically, the canting angle γ will be larger than 0°, and may, but does not need to, reach $\gamma_{max}$.

It is an important aspect of the present invention that the arc wire, i.e., e.g., the wavy wire or the canted coil spring, is firmly fixed such that upon application of a force generally along the z-direction of the arc, there is very little, if any movement possible between the pinch points and the support. Thus, the lower portions of the arc wire that may rest on the support are prevented from flexing and twisting.

This can be suitably achieved by a pinching device that applies a width directional compression to the arc wire. In case of the canted coil this essentially reaches its maximum canting angle $\gamma_{max}$, and the side portions of two adjacent turns are essentially force-fittingly compressed towards each other at a pinch-point 140, such as by being in direct contact with each other and held firmly in this position by the pinching device that also serve for affixing the canted coil spring on the operating drum or roll. The compression force of the compression jaws is adjusted according to the intended use, and for applications, where higher z-directional forces are exerted, also the compression forces should be adapted accordingly so as to keep the wires affixed at the pinch points by the corresponding pinch force. A skilled person will readily realize, that the term "direct contact" includes variants, where something is placed between the wires and/or the compression jaws, such as a spacer, that transmits the forces.

Suitable pinching device may be any means that apply a compression along the width or y-direction of the arcs, most preferably constant along the length of the canted coil spring. A pinching device may be positioned on the surface of the support roll or may be integral with the support roll, the being position outwardly of the remaining surface.

The plurality of arcs may be mounted essentially at any position and orientation on a base drum or roll. However, the fixation can be easily executed, when it is in either an axial or a radial orientation, as explained in the context of FIGS. 7 and 9. Generally, a roll exhibits in cylindrical coordinates a radius r 70, an angular coordinate φ (phi) 50, and a width coordinate λ (lambda) 60.

Figures 7A, 7B:
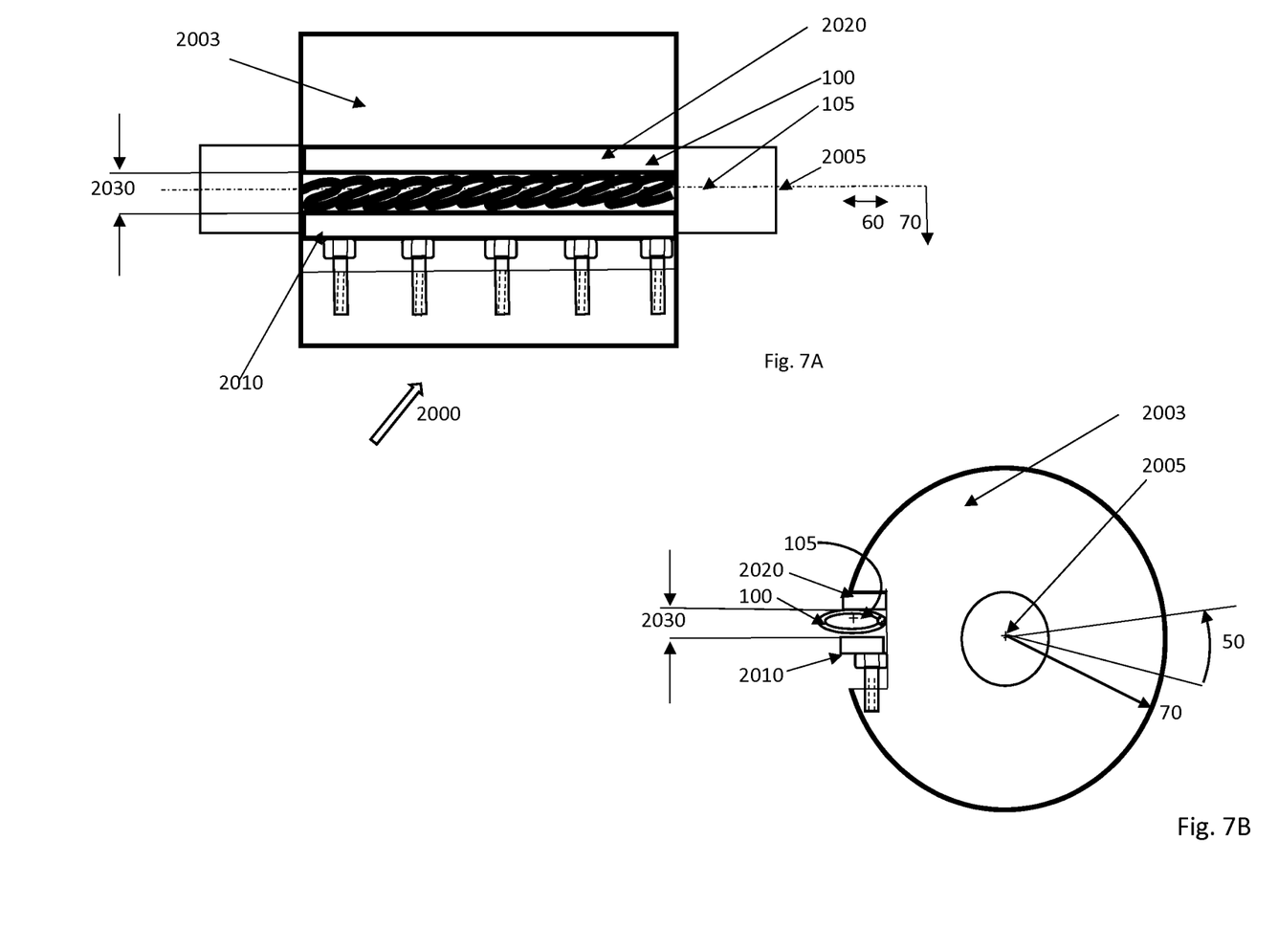

Referring to FIGS. 7A and B, an axially positioned arc wire, here shown as an axially canted coil spring 100 is placed on a base roll 2003, with a coil axis 105 essentially parallel to the roll axis 2005. The anvil roll 2000 further comprises a first (2010) and a second (2020) compression jaw at a predetermined and optionally adjustable spacing 2030 that corresponds to the width of the canted coil at maximum canting angle at which side portions of two adjacent turns are held in direct contact by the compression jaws.

Figure 8A:
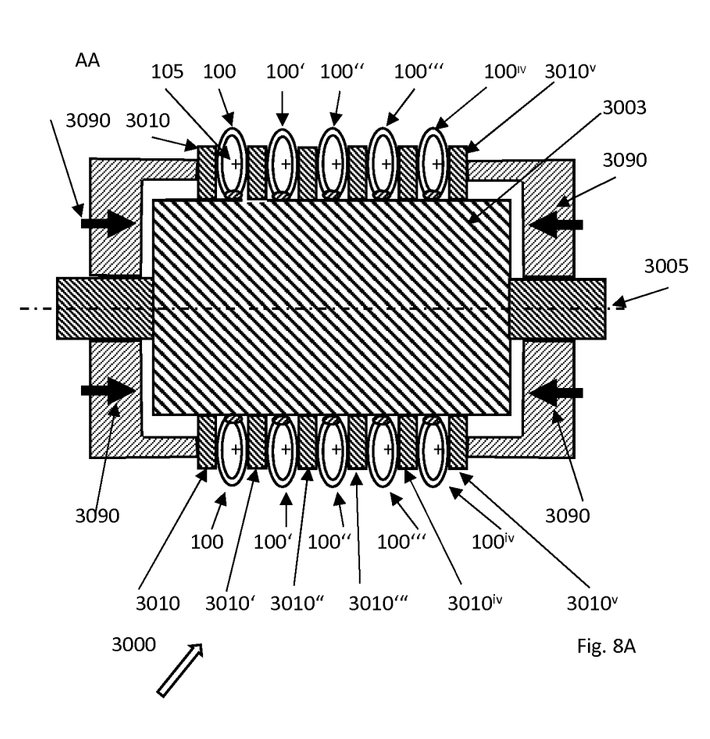
FIGS. 8A and B depict another execution of an anvil roll comprising a canted coil spring according to the present invention.
Figure 8B:
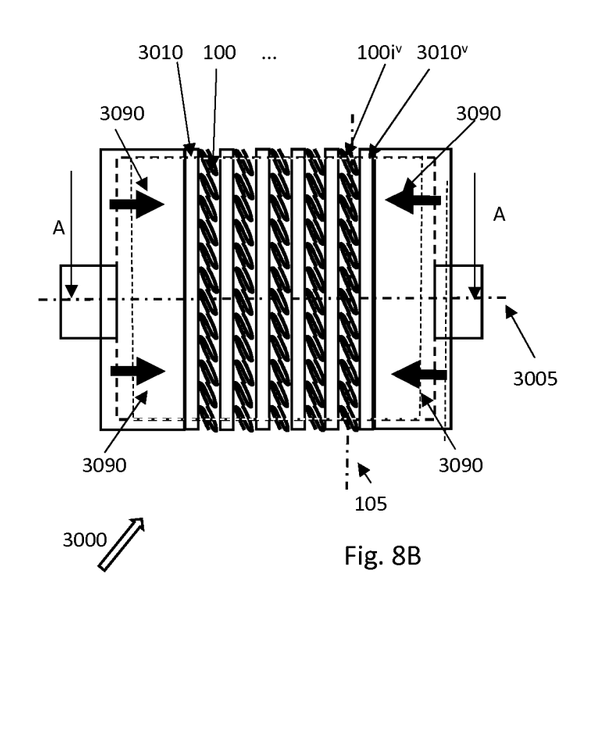
Figure 9A:
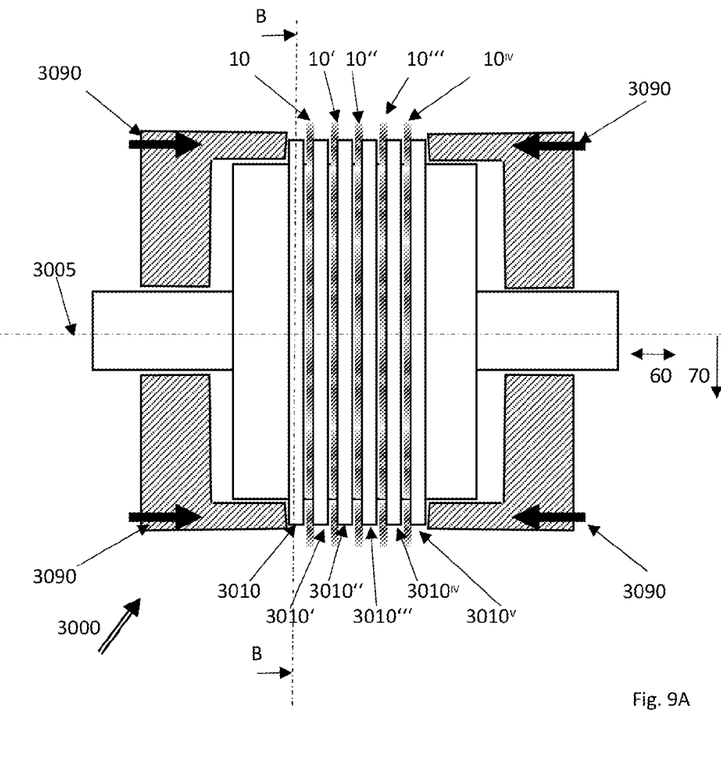
FIGS. 9A and B depict another execution of an anvil roll comprising a canted coil spring according to the present invention.
Figure 9B:
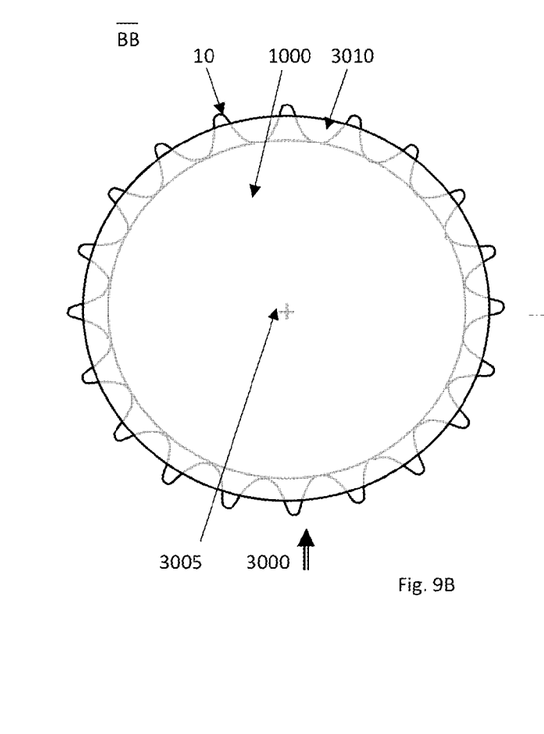

Referring to FIGS. 8 and 9, a set of arc wires may be circumferentially arranged on an anvil roll 3000. In FIGS. 8A and B, this is depicted for canted coil springs, here shown exemplarily and non-limiting with five coil springs, 100, 100', 100'', 100''', and 100$^{iv}$ each one between a pair of compression jaws, 3010, 3010', 3010'', 3010''', 3010$^{iv}$, 3010$^{v}$. The jaws may be fixed protrusions extending from the surface (not shown), they may be unique parts of the anvil roll (not shown), or may also be circumferential rings, that may be mounted axially moveable on the roll, and which may be compressed by a compression tool, here indicated with arrows 3090, as may be threaded bolts pulling caps on one or both sides against the anvil roll. Analogously, FIGS. 9A and B depict such an anvil roll with wavy wires 10, 10', . . . compressed by pinching device 3090 and separated by disks 3010, 3010', 3010'', etc.

The compression jaws may be particularly adapted to enhance the fixation of the arc wire. This may be achieved by exhibiting a jaw height, i.e. the height of the jaws over the support surface, is at least the height of pinch points 40, 140. The jaws may also be tapering z-directionally, such that at the lower part they allow for a minimum distance between them, e.g., of twice the coil wire diameter to allow for the wire overlap at a pinch point, to once a coil wire diameter more upwardly, where the wire portion would be even more fixed.

When referring to the positioning of the arc wire and the compression jaws "in" or "on" the base roll, it includes designs where the base roll may not have a smooth surface, but may have surface structures such as notches or grooves or other cavities, but also elevations such as rings, pins and the like, and such structures may also function as a part of the compression jaws.

In a particular execution, the support surface oriented portion of a canted coil spring may suitably be levelled to a high precision, such as by inverting the orientation, i.e. positioning the arc portion that is outwardly oriented on the roll in the in-use configuration, onto an auxiliary support surface, and machining the then outwardly oriented portions of the arc wire to the desired accuracy, prior to re-assembling the arc wire onto the anvil roll.

An arc wire may be adapted to its intended use by
selecting the height (e.g. by selecting the outer diameter of a pre-cursor spring);
selecting the wire diameter;
selecting the wire material;
selecting the arc distance respectively the coil spring pitch;
selecting the overall pattern by selecting:
the number,
the orientation,
the length
of the arc wire;
selecting the acceptable variation of the dimensions, especially height and wire diameter.

For certain applications, such as when performing bonding operation with the anvil roll, and even more so when the bonding operation is using ultrasonic energy, it is preferred that the height differences of the turns of the canted coil spring or wavy wire are small. For ultrasonic applications, the height differences are preferably below the amplitude of the ultrasonic horn, as often is about 18 µm or less. Thus preferably the variation of the height of the coil spring is lower than about 18 µm and preferably less than about 10 µm or even less than 5 µm.

Thus, to this end, a pre-formed canted coil spring or wavy wire may be affixed on the surface of an anvil base roll 2003, 3003 in FIGS. 7 and 8, whilst the compression jaws are compressed at an adjustment pinch force to hold the canted coil spring in place, but still allowing a relative movement of the wires at the pinch points upon exerting a z-directional force onto the protrusions. An auxiliary support tool (not shown in the figures), flat or concavely opened towards the spring/wire and at a sufficient length to cover several, preferably all of the turns of the canted coil spring or wavy wire, is positioned over and pressed downwardly, i.e. along the z-direction of the spring/wire. Thereby, height differences of the turns/windings are levelled, and the compression jaws are tightened to fix this positioning, until the ultimate pinch force, that is required to withstand the operational z-directional forces, has been reached. Optionally, these steps may be repeated with increasing downward pressure of the auxiliary tool and increasing compression of the jaws. Instead of using an auxiliary support tool, the anvil roll may be put in operation, e.g., when running against a counter tool, such as a flat or rotatable roll, whilst the compression of the jaws is at a moderate level. The operation will level the height differences, and the compression may gradually be increased, until the ultimate pinch force is reached.

In an alternative approach for adjusting the height of the turns, a canted coil spring may be "inverted", i.e. positioned with the uppermost point in the in-use configuration downwardly on an auxiliary surface, to then precision machining the then outwardly positioned region. Thereafter, the canted coil spring can be positioned with the precision grinded portions on the anvil base roll.

EXAMPLE

In an exemplary execution, a non-canted per-cursor helical spring of conventional stainless steel exhibiting a length of approximately 100 mm, an outer diameter of 14 mm and a wire diameter of 1 mm was canted and affixed on a bench vise support between two metal jaws to its minimum width, exhibiting a pitch of about 14 mm. The jaws extended to about 60% of the spring coil height.

Two layers of spunbonded polypropylene webs of approximately 19 $g/m^2$ and as are typically applied as topsheet material in hygiene articles, were placed over the free protrusions of the canted coil spring and treated with a conventional hand-held ultrasonic bonding sonotrode, such as available from Herimann Ultraschall, DE.

The result was a very smooth, soft, and strongly holding line of bond points and no movement relative to the support was observed.

The same experiment was repeated with a softer spring exhibiting an outer diameter of 20 mm and a wire diameter of 0.75 mm, with the same results regarding spring movement relative to the support.

The invention claimed is:

1. An anvil roll, for treating a web material,
exhibiting a cylindrical outer support surface, an anvil roll axis, a radius,
comprising
a plurality of arcs protruding outwardly of said cylindrical outer base surface,
said arcs being formed by an arc wire,
said arcs comprising
an upper free arc portion oriented outwardly of said support surface
such that the surface of said arc wire tapers down from its tip as the most outwardly positioned point of said free arc portion towards said anvil roll support surface in all directions,
a first and a second side arc portion,
wherein said plurality of arcs is arranged such that
an arc tip line connecting said most outwardly positioned points of said upper arc portions defines the x-direction of said arcs,
wherein each arc exhibits a length extension ($x_H$) along x-direction and a free arc height $H_0$ extending perpendicularly to said support surface and to said length extension $x_H$, said anvil roll further comprising a pinching device comprising at least two compression jaws positioned radially outwardly of said support surface, and adapted to apply a transverse compression force along a y-direction perpendicular to said length and height extension of said arcs at a pinch point in said side portions of said arcs,
thereby essentially preventing movement of said arc wire in said pinch point,
said pinching device further being adapted to transmit z-directional forces applied to said upper arc portion and via said first or second side portion through the pinch point to said support surface.

2. An anvil roll according to claim 1, wherein said arc wire exhibits a rounded cross-section.

3. An anvil roll according to claim 1, wherein said arc wire exhibits a cross-section that extends at least at said most outwardly positioned points of said upper arc portions in the y-direction of said arc between 0.1 mm and 5 mm.

4. An anvil roll according to claim 1, wherein the upper arc portion is circumscribed by an x-, z-directionally spanned circle of between 0.2 and 50 mm.

5. An anvil roll according to claim 1, wherein a distance in the x-direction of said most outwardly positioned points of said upper arc portions is more than 0.1 times said free arc height $H_0$.

6. An anvil roll according to claim 1, adapted to withstand z-directional impact on the arcs under use conditions such that these deform z-directionally less than 20 μm.

7. An anvil roll according to claim 1, wherein one of the conditions applies that are selected from the group consisting of
 a. the arc wire is pinched at a single pinch point wherein two wires are crossing;
 b. the arc wire is pinched at two pinch points or pinch areas, each one in each of said side portions wherein a single wire is pinched;
 c. the arc wire is pinched at three pinch points, with two pinch points in said side portions, wherein two crossing wires are pinched, and a single pinch point wherein two wires are crossing, the single pinch point being positioned between the other two pinch points and the support surface; and
 d. the arc wire is pinched such that each two directly neighboring arcs have two common pinch points.

8. An anvil roll according to claim 1, wherein said arc wire is essentially continuous for said plurality of arcs.

9. An anvil roll according to claim 1, comprising two or more arc wires, preferably aligned parallel to each other.

10. An anvil roll according to claim 1, wherein said arc wire is selected from the group consisting of
 a. a canted coil spring; and
 b. a wavy wire.

11. An anvil roll according to claim 1, comprising two or more wavy wires positioned parallel between one pair of compression jaws and such that their tip lines are essentially parallel and their tip points are x-directionally offset.

12. An anvil roll according to claim 1, wherein said x-direction of said arc wire is essentially aligned with the direction selected from the group consisting of:
 c. parallel to said anvil axis or circumferentially to said anvil surface.

13. An anvil roll according to claim 1 for ultrasonic bonding.

14. An anvil roll according to claim 1, wherein said arcs being formed by a metallic wire.

15. An anvil roll according to claim 2, wherein said arc wire exhibits a circular or elliptic cross-section.

16. An anvil roll according to claim 5, wherein a distance in the x-direction of said most outwardly positioned points of said upper arc portions is more than 1.0 times said free arc height $H_0$.

17. An anvil roll according to claim 6, adapted to withstand z-directional impact on the arcs under use conditions such that these deform z-directionally less than 10 μm.

18. An anvil roll according to claim 12, wherein said compression jaws are ring discs, or disc elements being integral parts of the anvil roll, and wherein said pinching device further comprises a compression means that is adapted to act on said compression jaws simultaneously.

* * * * *